US005747002A

United States Patent [19]
Clark et al.

[11] Patent Number: 5,747,002
[45] Date of Patent: May 5, 1998

[54] PREPARATION OF SODIUM CHLORIDE AEROSOL FORMULATIONS

[75] Inventors: Andrew Reginald Clark, Half Moon Bay; Chung C. Hsu, Los Altos; Andrew J. Walsh, San Francisco, all of Calif.

[73] Assignee: Genentech, Inc., So. San Francisco, Calif.

[21] Appl. No.: 416,998

[22] Filed: Apr. 5, 1995

[51] Int. Cl.$^6$ .................................................. A61K 9/12
[52] U.S. Cl. ........................... 424/45; 424/46; 424/489; 424/680; 514/937; 514/951
[58] Field of Search ........................ 424/45, 46, 489, 424/680; 514/937, 951

[56] References Cited

U.S. PATENT DOCUMENTS

| | | | |
|---|---|---|---|
| 2,533,065 | 3/1950 | Taplin et al. | 424/45 |
| 4,009,280 | 2/1977 | Macarthur et al. | 424/45 |
| 5,478,578 | 12/1995 | Arnold et al. | 424/45 |

FOREIGN PATENT DOCUMENTS

| | | |
|---|---|---|
| 11746 | 6/1993 | WIPO . |
| 22993 | 8/1995 | WIPO . |
| 28944 | 11/1995 | WIPO . |

OTHER PUBLICATIONS

Hickey, A.J. and N.M. Concessio, "Flow Properties of Selected Pharmaceutical Powders from a Vibrating Spatula," *Part. Part. Syst. Charact.*, 11:457–462 (1994).

Hickey et al., *Pharmaceutical Technology* pp. 58–82 (1994) "Factors influencing the dispersion of dry powders as aerosols".

Hargreave et al., *J. Allergy Clin. Immunol.*, 68(5) pp. 347–355 (1981) "Bronchial responsiveness to histamine or methachloine in asthma: measurement and clinical significance".

Smith et al., *J. Allergy Clin. Immunol.*, 84(5) pp. 781–790 (1989) "Inhalation provacation tests using nonisotonic aerosols".

Gennaro, A.R. (1985) Remington's Pharmaceutical Sciences. Mack Pub. Co., pp. 1585–1588.

Ansel, H. C. et al. (1995). Pharmaceutical Dosage Forms and Drug Delivery Systems. Williams & Wilkins, pp. 255–259.

*Primary Examiner*—Raj Bawa
*Attorney, Agent, or Firm*—Flehr Hohbach Test Albritton & Herbert LLP

[57] ABSTRACT

Disclosed herein is a method for the preparation of sodium chloride formulations having a substantially uniform particle size suitable to ensure the dispersible properties for inhalation into the lungs of a subject. The formulations thus prepared are also the subject of this disclosure. The method involves jet milling coarse sodium chloride in one or preferably two or more procedures using air pressure suitable to produce particles having a significant fraction that are less than about 7 microns in size. Immediately following the milling, the particles are vacuum dried in an oven using a temperature and time suitable to cure the product to prevent substantial aggregation over time.

7 Claims, 1 Drawing Sheet

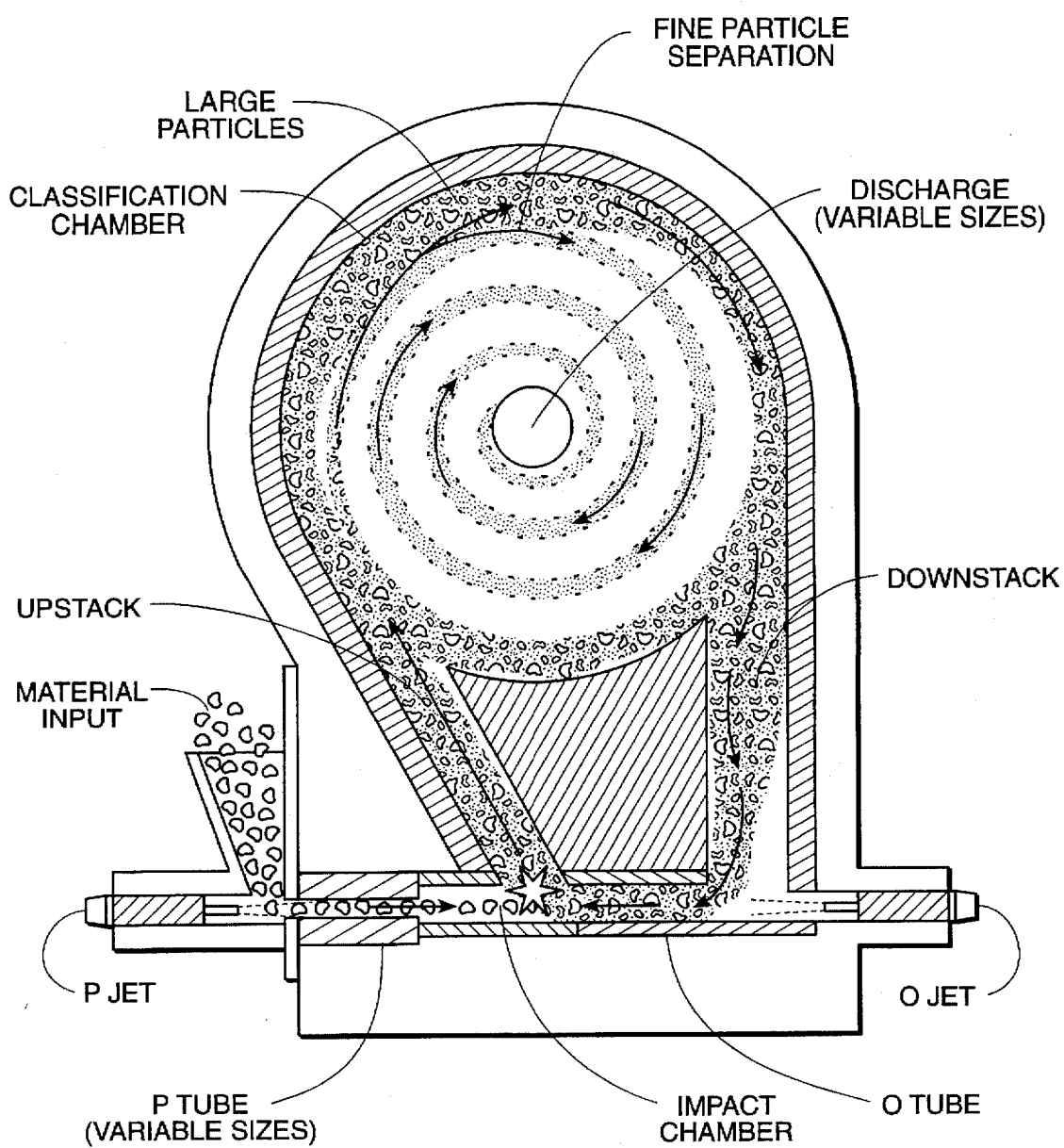
FIG._1

5,747,002

PREPARATION OF SODIUM CHLORIDE AEROSOL FORMULATIONS

FIELD OF THE INVENTION

The present invention is directed to the preparation of formulations containing dispersible salt particles that are suitable for aerosol administration to man. It is directed as well to the finished pharmaceutical preparations.

BACKGROUND OF THE INVENTION

Dry powders and their delivery devices are an alternative to pressure-packed propellant-driven systems for the administration of aerosols to the lung in order to obtain biological effect by systemic absorption in the lung. However, further developments are needed in the technology required to disperse dry powders as aerosol if there is to be an alternative to propellant-driven systems as a primary means of aerosol delivery.

For such progress to occur, of primary importance are the morphological characteristics of the particles themselves. Thus, in order to be assured of dispersal of the particles into the lung airway passages such that they approach the alveoli of the lung, the particles must be of a particle size of less than about 7 microns. In addition, the preparations must have a high percentage of dispersible particles.

Because of this, the preparation of the particles is of especially critical importance. For example the particles if not prepared properly may interact with each other and with surrounding surfaces thus forming aggregation with consequential increases in particle size and reduced dispersibility. Among the underlying forces giving rise to these interactions among the particles during their preparation are electrostatic charge, Van der Waals, capillary and mechanical or interlocking forces.

The interparticulate forces are mostly attractive and cause cohesion of particles to each other and adhesion to the surfaces they encounter. For the fine particles required for aerosol delivery to the lung, these forces are most pronounced and extremely difficult to overcome. As the particle size decreases, with the goal of being small enough to be available within the lung, dispersion becomes increasingly difficult because of the aforementioned forces that lead to increased energies of association. With time this high energy state is reduced but it is often accompanied by aggregation of the particles which in turn reduces dispersibility and increases particle size. For further background information, see Hickey et al., *Pharmaceutical Technology*, Page 58 et sequence. (August 1994).

Asthma is a chronic inflammatory disease of the airways. The airways of asthmatics are particularly sensitive to a wide variety of chemical, physical and allergenic stimuli. The sensitivity is manifested by a narrowing of the airways with a reduction in the forced expiratory volume.

Bronchial provocation testing, and measuring changes in the forced expiratory volume in response to inhaled stimuli, is relatively well established as a technique for identifying and assessing the severity of airway hyper-responsiveness in persons suspected of having asthma. A number of provocative agents are available and include histamine and methacholine. These are believed to act directly on specific receptors in the airways causing bronchial smooth muscle contraction. See Hargreave et al., *J. Allergy Clin. Immunol.*, 68,347 (1981) and Smith et al., *J. Allergy Clin. Immunol.*, 84, 781 (1989).

It was recognized years ago that the airways of asthmatics are sensitive to the loss of water from the respiratory tract when large volumes of air need to be humidified to body conditions during hyperventilation brought on for example by exercise. This hypothesis prompted the development of a bronchial provocation test using an aerosol of sodium chloride.

However, for the reasons mentioned above, the preparation of aerosols that would prove suitable for delivery into the lung in such provocation tests proved difficult. The presently practiced provocation tests uses wet aerosols of salt requiring the use of a nebulizer. It would be considered particularly advantageous if one could administer the provocative agent to a subject in the form of a dry powder rather than a wet aerosol. It could for example be administered via a conventional inhaler rather than through a nebulizer.

Thus, it was an object of the present invention to produce preparations of sodium chloride that would have the right particle size and dispersibility characteristics such that the preparation could be inhaled with a simple inhaler and reach the airways of the lung for such provocation use. As used in this invention the term "airways" include both the upper airways, the naso or oropharynx, but more particularly the lower airways, the tracheobronchial and pulmonary regions of the lung.

SUMMARY OF THE INVENTION

The present invention is directed to a method of preparing pharmaceutical preparations of sodium chloride in the form of dispersible particles in a respirable size range. In the present context, the term "dispersible particles" refers to the characteristics of the sodium chloride preparations that enable assurance that the sodium chloride will be a free flowing preparation of more or less reproducible, constant particle size. It has been determined that a particle size distribution with a significant fraction of particles less than about 7 microns in size is necessary to assure delivery of the sodium chloride into the lower airways of the lung. In the present context, the term "respirable size range" refers to the same criterion referred to above in respect of assurance of delivery of the sodium chloride into the lower airways of the lung.

The present invention is predicated on the finding that in order to produce sodium chloride preparations meeting the criterion of being dispersible in a respirable size range, preparation procedures are important criteria.

The method of the present invention comprises the steps of jet milling the particles in a suitable, conventional milling apparatus using air pressure suitable to produce particles having a significant fraction that are less than about 7 microns in size. It has been found that the milling procedure is preferably conducted twice consecutively to increase the fraction of particles less than about 7 microns in size. After the milling the sodium chloride milled preparation is then vacuum-heated at a time and temperature sufficient to "cure" the sodium chloride preparation without the side effect of aggregation of particles.

It has been found that the high energy state existing within the particles after the jet milling is restored with time but only at the expense of considerable aggregation causing the preparation to be unsuitable for administration as set forth above. It was found that immediate vacuum heating causes a restoration of the lower energy states without such aggregation.

Stated another way, the present invention is directed to a method of preparing dispersible particles of sodium chloride in a respirable size range which maintain their dispersibility and size overtime comprising the steps of jet milling sodium chloride in one or preferably two or more separate procedures followed immediately by vacuum drying of the jet milled preparation. The conditions of jet milling is to use a conventional milling apparatus using an air pressure suitable to produce particles having a significant fraction that are less than about 7 microns in size. The vacuum oven heating is conducted at a temperature and time sufficient to cure the product to prevent substantial aggregation over time. Air pressure of about 20 pounds per square inch gauge at the entrance of the mill is a reasonable lower limit for the mill used in the current preparations. Different sized mills may have a larger or smaller minimum pressure requirement. Temperature of about 140° C. for about 30 minutes are reasonable lower limits for the baking temperature and duration. Although lower temperatures and shorter times may be sufficient, better results are more likely at higher temperatures and longer times. The temperature must not exceed the melting temperature of the solid, 801° C. for NaCl. At temperatures approaching the melting point, long exposure may cause degradation of the product.

The present invention is also directed, as a second aspect, to a pharmaceutical preparation comprising sodium chloride in the form of dispersible particles in a respirable size range.

The powder is then packaged in vials suitable for transport and then filled into hard gelatin capsules for delivery via an inhaling device for use in bronchial provocation testing.

BRIEF DESCRIPTION OF THE DRAWING

FIG. 1 depicts a micronizer (jet milling apparatus) suitable for preparing the sodium chloride preparations of the present invention via the two-step milling procedure defined above and described in more detail below.

DETAILED DESCRIPTION

The preparative steps herein employed sodium chloride. However, the process may be useful for other crystalline solids for which micronization provides sufficient energy to disrupt the crystal lattice. For example, potassium chloride, or lithium chloride could be used.

Materials and Methods

Preparation of Sodium Chloride Powder by Micronization (Jet Milling)

Micronization of sodium chloride crystals was done using a Trost jet mill as shown in the accompanying figure. The jet mill operates using compressed nitrogen gas split into two lines which enter at opposite sides of the mill. The material to be milled is fed into one of the streams and travels up into the mill. Larger particles settle back to the bottom where they collide with incoming material and break up. Smaller particles exit in the gas stream through a hole in the back of the mill, travel through a cyclone and are deposited in a flask. Very fine particles are retained in a depository bag at the end of the line. Sodium chloride was AR grade from Mallinckrodt.

Prior to milling, all parts of the mill were washed with milli-Q water, rinsed with ethanol and dried under a stream of nitrogen. Coarse sodium chloride crystals were ground with a mortar and pestle and then fed into the micronizer operating at approximately 60 pounds per square inch on both nitrogen lines. The powder was collected from the flask and cyclone and then remilled. The twice-milled powder was collected and dried in the vacuum oven on a watch glass at approximately 176° C. and 20 inches mercury vacuum. After about 1 hour of vacuum heating, the powder was filled into vials. After filling, each vial was capped, sealed and placed in a desiccator.

Micronization proved to be effective at producing a significant fraction of redispersible, respirable particles when the sodium chloride was milled twice and baked in the vacuum oven as set forth above. The particle size distribution after dispersion was measured by aerosolizing the powder into a multiple stage liquid impinger from a conventional inhaler. Results for the initial, two week, and six month time points are shown below. The error in each value is approximately ±10% of the value.

| particle size range | % of dispersed particles initially | % of dispersed particles after 2 week | % of dispersed particles after 6 months |
|---|---|---|---|
| ≥20 μm | 6.5 | 9.9 | 8.8 |
| 10 ≤ X < 20 μm | 41.0 | 38.5 | 39.9 |
| 7 ≤ X < 10 μm | 15.9 | 15.1 | 16.8 |
| 3 ≤ X < 7 μm | 28.6 | 28.1 | 27.4 |
| <3 μm | 7.8 | 8.4 | 7.1 |

The total fraction of particles in the respirable size range, less than about 7 μm, is calculated by adding the last two rows in the table above. For the initial, two week, and six month time points the respirable fractions are 36.4%, 36.5%, and 34.5%, respectively. The error in each value is approximately 3.0%.

The sodium chloride preparations were administered to human subjects using the same conventional inhaler as that used for dispersibility measurements above. Specifically, the Halermatic by Fisons was employed. The results of this study demonstrated that the sodium chloride preparations delivered from a capsule via an inhalation device, can provoke airway narrowing in the same asthmatic subjects who are sensitive to the wet aerosol preparation of saline. Although the number of subjects studied was small, there was a good correlation in the range of severity of asthma as compared with the same subjects administered a wet aerosol. There were no untoward side effects.

Three batches of respirable NaCl powder were prepared by the same method as that used above to test the reproducibility of the method. The method involved jet milling twice and subsequent baking at approximately 176° C. and 20 in. Hg vacuum for one hour. The batches were prepared consecutively following the same procedure with one exception. Between the first and second batches, the mill was disassembled and wiped clean with a paper towel. Between the second and third batches, however, the mill was not cleaned.

The respirable fraction of each powder was measured. The results for the initial, two week, and four week time points are shown below.

| | Mass prepared (g) | Respirable fraction initially | Respirable fraction after 2 weeks | Respirable fraction after 4 weeks |
|---|---|---|---|---|
| Batch 1 | 5.8 | 30.5 | 35.1 | 33.2 |
| Batch 2 | 6.3 | 28.2 | 27.0 | 33.9 |
| Batch 3 | 8.0 | 31.5 | 33.5 | 31.8 |

The results indicate that the respirable fraction is not decreasing in any of the batches. The error in each value is approximately ±3%. The cleaning step between batches 1 and 2 does not appear to be relevant.

Concluding Remarks

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims.

All documents cited herein are hereby expressly incorporated by reference herein.

We claim:

1. A method of preparing pharmaceutical preparations of sodium chloride in the form of dispersible particles for aerosol delivery to the lungs comprising the steps of jet milling sodium chloride followed immediately by vacuum drying in an oven to prevent aggregation of the jet milled preparation, wherein said pharmaceutical preparations comprise dispersible particles of sodium chloride of less than about 7 microns in size.

2. The method according to claim 1 wherein the jet milling is conducted at least twice consecutively.

3. The method according to claims 1 or 2 wherein in the jet milling procedure, the air pressure supplied produces sodium chloride particles less than about 7 microns in size.

4. The method according to claim 1 or 2 wherein the vacuum drying is conducted at a temperature in the range of about 140° C. to 801° C.

5. The method according to claim 3 wherein said air pressure is at least 20 psig.

6. The method according to claim 1 wherein the vacuum drying is conducted for about 30 minutes to about 1 hour.

7. The method according to claim 6 wherein said time ranges from at least 30 minutes based on an oven temperature of at least 140° C.

* * * * *